United States Patent
Kang

(10) Patent No.: US 7,090,649 B2
(45) Date of Patent: Aug. 15, 2006

(54) TOTAL SKIN MANAGEMENT SYSTEM AND TOTAL SKIN MANAGEMENT METHOD USING THE SAME

(75) Inventor: Hyun Song Kang, Seoul (KR)

(73) Assignee: Hwajin Cosmetics Co., Ltd., Seoul (KR)

( * ) Notice: Subject to any disclaimer, the term of this patent is extended or adjusted under 35 U.S.C. 154(b) by 542 days.

(21) Appl. No.: 10/365,199

(22) Filed: Feb. 11, 2003

(65) Prior Publication Data

US 2003/0163068 A1   Aug. 28, 2003

(30) Foreign Application Priority Data

Feb. 23, 2002 (KR) .................... 10-2002-0009748
Mar. 14, 2002 (KR) ................ 20-2002-0007549 U
Mar. 14, 2002 (KR) ................ 20-2002-0007550 U

(51) Int. Cl.
*A61H 23/00* (2006.01)
*A61N 1/18* (2006.01)

(52) U.S. Cl. .................... 601/2; 601/15; 601/46; 607/100; 607/94; 607/145; 607/150; 607/3

(58) Field of Classification Search ............ 601/4, 601/15, 17, 21
See application file for complete search history.

(56) References Cited

U.S. PATENT DOCUMENTS

| | | | | |
|---|---|---|---|---|
| 2,745,400 A * | 9/1956 | Mueller et al. | ............... | 601/15 |
| 2,830,578 A * | 4/1958 | Degroff | ........................ | 601/21 |
| 5,101,809 A * | 4/1992 | Daffer et al. | ................. | 601/52 |
| 5,690,608 A * | 11/1997 | Watanabe et al. | ............ | 601/19 |
| 6,007,502 A * | 12/1999 | Lee | .............................. | 601/17 |
| 6,022,327 A * | 2/2000 | Chang | ......................... | 601/15 |
| 6,443,978 B1 * | 9/2002 | Zharov | ........................ | 607/91 |
| 6,743,215 B1 * | 6/2004 | Bernabei | .................... | 604/500 |
| 2003/0060743 A1 * | 3/2003 | Chang | ......................... | 601/162 |
| 2004/0236252 A1 * | 11/2004 | Muzzi et al. | .................. | 601/1 |
| 2005/0107849 A1 * | 5/2005 | Altshuler et al. | ............. | 607/88 |

FOREIGN PATENT DOCUMENTS

DE           29717774 U1 * 11/1997

* cited by examiner

*Primary Examiner*—Danton DeMille
(74) *Attorney, Agent, or Firm*—Dellett & Walters

(57) ABSTRACT

The present invention relates to a skin management system, and in particular to a total skin management system and a total skin management method using the same which are capable of checking a state of skin and comprehensively managing a skin based on a type of skin. In addition, the present invention relates to a total skin management system and a total skin management method using the same which are capable of checking a state of skin and classifying the skin into numerous types by integrating and controlling the functions of a skin check, far infrared ray massage, ozone massage, low frequency massage, low frequency vibration massage and ultrasonic wave massage and comprehensively managing the functions of a skin cleansing, skin management, skin nutrition and skin elastic force increase through a certain skin exercise corresponding to a structure of skin based on a skin cell activity and metabolism in a proper combination with the functions of an infrared ray massage, ozone massage, low frequency wave massage, low frequency vibration massage and ultrasonic wave massage based on the checked type of skin.

17 Claims, 12 Drawing Sheets

300

400

500

700

TOTAL SKIN MANAGEMENT SYSTEM AND TOTAL SKIN MANAGEMENT METHOD USING THE SAME

BACKGROUND OF THE INVENTION

1. Field of the Invention

The present invention relates to a skin management system, and in particular to a total skin management system and a total skin management method using the same which are capable of checking a state of skin and comprehensively managing a skin based on a type of skin, and further relates to a total skin management system and a total skin management method using the same which are capable of checking a state of skin and classifying the skin into numerous types by integrating and controlling the functions of a skin check, far infrared ray massage, ozone massage, low frequency massage, low frequency vibration massage and ultrasonic wave massage and comprehensively managing the functions of a skin cleansing, skin management, skin nutrition and skin elastic force increase through a certain skin exercise corresponding to a structure of skin based on a skin cell activity and metabolism in a proper combination with the functions of an infrared ray massage, ozone massage, low frequency wave massage, low frequency vibration massage and ultrasonic wave massage based on the checked type of skin.

2. Description of the Background Art

Since the history of human begins, the pursuit concerning beauty has been continued together with the dignity of human without stops as the most acutely natural desire of human.

The above desire for the beauty begins based on an effort for implementing a healthier and clean skin. Since the skin is directly affected by an external stress, in order to obtain a beautiful skin, the skin must be intensively cared, and the skin must be often checked.

However, a certain skin management method may damage the skin without a professional knowledge concerning the skin. The skin is delicate and sensitive, so that the skin is deemed as a barometer by which it is possible to directly check the state of health and trace of aging.

Therefore, the states of the delicate and sensitive skin must be often checked, and a proper skin management must be performed based on the state of skin. In order to effectively implement the above management, a certain skin management instrument is needed so that the damaged skin is improved.

In the conventional arts, as a beauty instrument capable of performing a massage with respect to a skin of face, there are known a far infrared ray jig capable of performing a blood way improvement function, an ozone jig capable of providing a tooth whitening function, an ion jig capable of providing a cleansing function and a vibration jig capable of providing a wrinkle prevention function.

However, the above far infrared ray massage or ozone and ion massage are separately implemented, so that only a simple impact is applied to the skin. In addition, since there is not provided an accurate skin checking unit by which it is possible to easily check the state of skin by a common user, it is impossible to accurately check the type of her/his skin, so that a proper skin management is not performed.

Furthermore, since the skin checking unit and the far infrared ray massage or ozone and ion massage are not comprehensively cooperated, even when her/his skin type is known, it is impossible to implement an efficient and comprehensive skin management based on the checked skin state.

SUMMARY OF THE INVENTION

Accordingly, it is an object of the present invention to provide a total skin management system and a total skin management method using the same which are capable of easily checking a state of skin by a user and providing a proper skin management method based on various modes corresponding to her/his skin type.

It is another object of the present invention to provide a total skin management system and a total skin management method using the same which are capable of comprehensively managing a skin based on her/his skin type by easily adjusting various skin management functions for managing her/his skin and properly combining the above functions.

It is still another object of the present invention to provide a total skin management system and a total skin management method using the same which are capable of implementing one combined system in which various beauty instruments are provided for thereby implementing a simple portability, so that it is possible to comprehensively perform a skin management based on a skin type by integrating and controlling the functions of a skin check, far infrared ray massage, ozone massage, low frequency wave massage, low frequency wave vibration massage, and ultrasonic wave massage.

In order to achieve the above objects, in a system for comprehensively managing a skin, a total skin management system comprises:

a low frequency wave jig which outputs a charge pulse for a skin check and a low frequency wave pulse for a low frequency wave massage;

a far infrared ray jig which outputs a far infrared ray by providing a far infrared ray lamp which is capable of outputting a far infrared ray;

a low frequency wave vibration jig which is formed of a vibration device for performing a low frequency wave vibration operation, and a vibration member which vibrates when the vibration device is driven based on a voltage inputted, and is symmetrically formed in parallel and operates as an auxiliary switch;

a purification jig which includes an ozone lamp for generating an ozone based on light and is capable of transferring a high voltage impulse to the ozone lamp and generating an ozone based on a ultraviolet ray of a certain wavelength;

a ultrasonic wave jig which includes a piezo-electric ceramic member for generating a vibration based on an input voltage and outputs a ultrasonic wave vibration;

a skin check driving unit which outputs a charge pulse for a reference resistance value through the low frequency wave jig for obtaining a reference resistance value and skin resistance value which are a basis to determine the type of skin;

a low frequency wave driving unit which is connected with a control unit through a connection terminal and includes an output terminal connected with the low frequency wave jig for thereby supplying a rated power to the low frequency wave jig;

a far infrared ray driving unit which is connected with the control unit through a connection terminal and is connected with the far infrared ray jig for thereby supplying a rated power to the far infrared ray jig;

a low frequency wave vibration driving unit which is connected with the control unit through a connection terminal and is connected with the low frequency wave vibration jig for thereby supplying a rated power to the jig;

an ozone driving unit which is connected with the control unit through a connection terminal and has an output terminal connected with the purification jig for thereby receiving a rated power and supplies a high voltage impulse for generating an ozone to the purification jig;

a ultrasonic wave driving unit which is connected with the control unit through an external connection terminal and has an output terminal connected with the ultrasonic wave jig for thereby supplying a rated power to the ultrasonic wave jig;

a key operation unit which includes various control keys and receives a user's key input signal;

a display unit which displays a corresponding operation corresponding to a key input of the key operation unit;

a memory which stores a program for a total skin management and various data;

a control unit which is formed of one chip microprocessor having a plurality of input/output terminals and performs a control operation in response to a key input from the key operation unit and displays a key input and a state and operation of the system based on the key input on the display unit and comprehensively controls the system; and a power supply unit which receives an alternating current power and supplies a rated direct current to the system and supplies a rated direct power for driving each element in accordance with a control of the control unit.

In order to achieve the above objects, in a method for comprehensively managing a skin using a total skin management system, a total skin management method comprises:

a skin state check step in which a face is cleanly washed, water is wiped away from the face, a skin check key is pressed, the type of the skin is classified into a dry type, neutral type, oily type using the low frequency wave jig, and a data is obtained for setting an operation time and operation intensity and function-based course of each mode;

a skin cleansing step in which a massage cream is uniformly applied over a face, a far infrared key is pressed, an operation time and operation intensity are adjusted based on the type of skin, the massage is smoothly performed from an inner portion to an outer portion, forming a circle, and when a selected operation time is passed, and an alarming sound is outputted, the cream is wiped out, and then the massage cream is uniformly applied over the face again, the purification key is pressed, the operation time and operation intensity are adjusted based on the type of skin, the massage is smoothly performed from an inner portion to an outer portion, forming a circle, and when a selected time is passed, and an alarming sound is outputted, the cream is wiped away using a water towel, and then the massage cream is uniformly applied over a whole portion of the face again, the low frequency wave key is pressed, the operation time and operation intensity are adjusted based on the type of skin, the massage is performed from a lower portion to an upper portion and from an inner portion to an outer portion along a skin pattern, and when the operation time is passed, and an alarming sound is outputted, the cream is wiped away using a steam towel;

a skin beauty step in which a gel cream is uniformly applied over the face, a low frequency wave(±) key is pressed, an operation time and operation intensity are adjusted based on the type of skin, the massage is performed from a lower portion to an upper portion and from an inner portion to an outer portion along a skin pattern, and when the operation time is passed and an alarming sound is outputted, the cream is wiped away using a water towel;

a skin beauty nutrition supply step in which a nutrition cream is uniformly applied over the face, a low frequency wave(+) key is pressed, an operation time and operation intensity are adjusted based on the type of skin, the massage is performed from a lower portion to an upper portion and from an inner portion to an outer portion along a skin pattern, and when the operation time is passed and an alarming sound is outputted, the cream is wiped away using a tissue; and a skip special management step in which a gel cream is uniformly applied over the face, a low frequency wave vibration key is pressed, an operation time and operation intensity are adjusted based on the type of skin, the massage is performed from a lower portion to an upper portion and from an inner portion to an outer portion along a skin pattern, and when the operation time is passed and an alarming sound is outputted, the cream is wiped away using a towel containing a warm water.

BRIEF DESCRIPTION OF THE DRAWINGS

The present invention will become better understood with reference to the accompanying drawings which are given only by way of illustration and thus are not limitative of the present invention, wherein.

| Descriptions of major elements of the drawings |
| --- |
| 10: total skin management system controller |
| 20: key operation unit |
| 30: display unit |
| 40: alarm unit |
| 50: timer |
| 60: memory |
| 100: total skin management system body |
| 110: skin check driving unit |
| 120: low frequency wave driving unit |
| 130: far infrared ray driving unit |
| 140: low frequency wave vibration driving unit |
| 150: ozone driving unit |
| 160: ultrasonic wave driving unit |
| 200: control/display panel unit |
| 201: skin check key |
| 203: far infrared ray key |
| 205: purification key |
| 207: low frequency wave (−) key |
| 209: low frequency wave (±) key |
| 211: low frequency wave (+) key |
| 213: low frequency vibration key |
| 215: start key |
| 217: ultrasonic wave key |
| 219: automatic key |
| 221: fuzzy key |
| 223: intensity adjusting key |
| 225: time adjusting key |
| 227: temporary stop/cancel key |
| 300: far infrared ray jig |
| 400: low frequency wave jig |
| 500: low frequency wave vibration jig |
| 600: purification jig |
| 700: ultrasonic wave jig |
| 800: exclusive cosmetics |
| 900: power supply unit |
| 1000: total skin management system |

DETAILED DESCRIPTION OF THE PREFERRED EMBODIMENTS

The preferred embodiments of the present invention will be described in detail with reference to the accompanying drawings. The same elements in the present invention will be given the same numeral references even when the elements appear in other drawings. In addition, the known functions and constructions which are not helpful for clarifying the gist of the present invention will be omitted.

The total skin management system according to the present invention is basically directed to a system implemented based on a mechanism in which a skin type is accurately checked, and a skin management corresponding to the checked skin type is comprehensively performed based on various functions such as a far infrared ray function, ozone function, low frequency wave function and low frequency vibration function.

In addition, the total skin management system according to the present invention is basically directed to performing the functions of a skin cleansing(deep cleansing), skin beauty(toning & firming), skin nutrition(suction nutrition) and skin elastic force increase.

Figure 1:
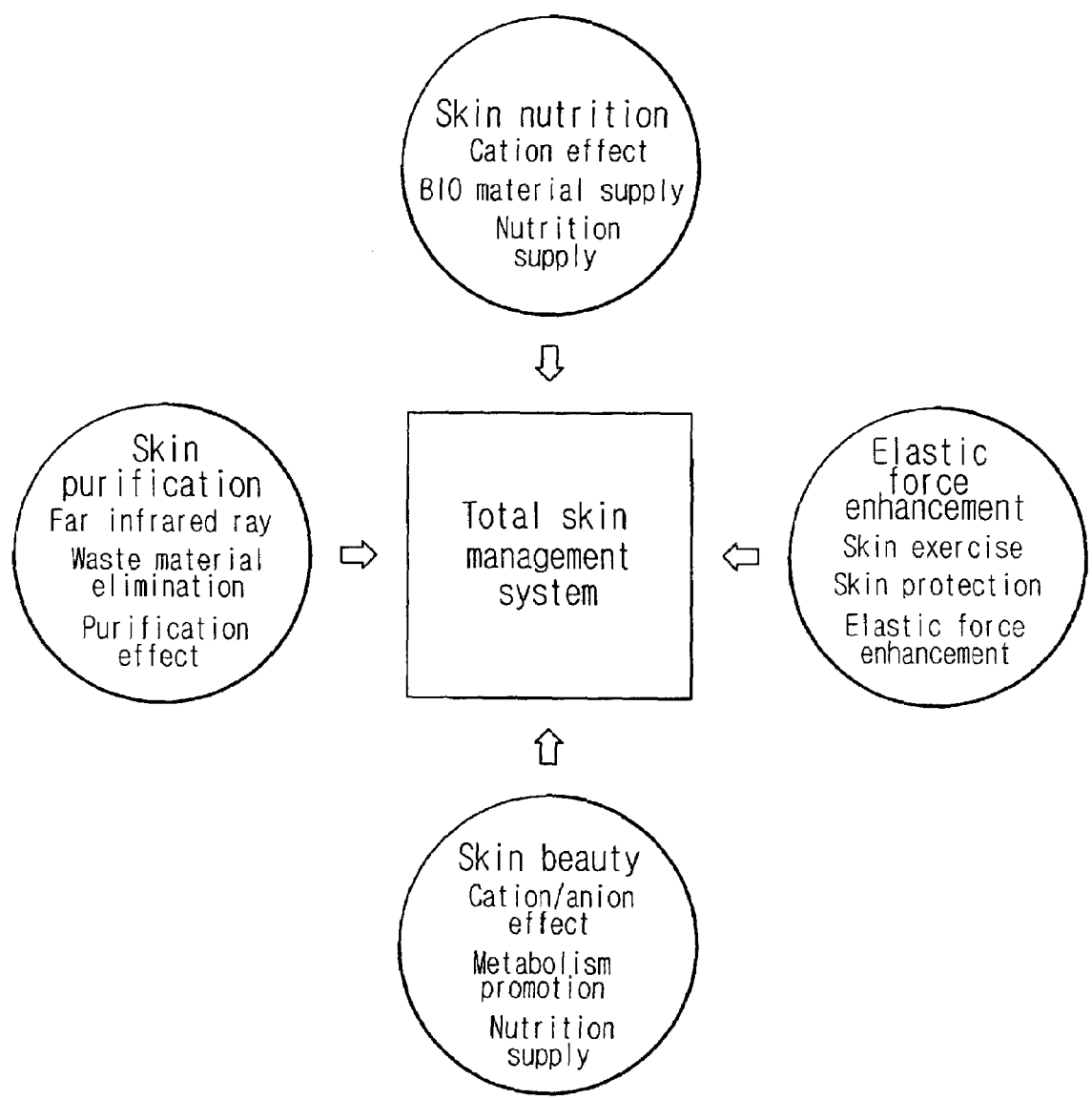
FIG. 1 is a view illustrating the functions implemented by a total skin management system according to the present invention.

The functions of the total skin management system according to the present invention are shown in FIG. 1.

FIG. 1 is a view illustrating the functions implemented in a total skin management system according to the present invention.

As shown in FIG. 1, the skin cleansing function is capable of dissolving, decomposing and eliminating waste materials from an outer skin and skin pores based on a far infrared ray, low frequency wave(−) and ozone purification effects. Therefore, the above skin cleansing function is capable of implementing a smooth and clean skin based on a skin peeling, cell exfoliation operation and purification function.

The above skin beauty function is capable of improving the skin to an elastic skin based on an exercise effect. In addition, the above skin beauty function is capable of improving the skin to a healthier skin based on a nutrition supply and making the skin elastic.

The above skin nutrition function is capable of basically increasing the elastic force of a skin structure and maintaining a young and beautiful skin. In addition, a metabolism is increased based on an increased fine circulation function, so that it is possible to implement a moisture skin.

The skin elastic force increasing function is classified into a lifting exercise and a ultrasonic function. The above skin exercise is capable of providing a skin damaged and aged by a polluted environment with a freshness and making the skin healthier. The above skin exercise function is capable of fully providing a skin with nutrition and increasing a skin elastic force based on a skin exercise effect.

In addition, the ultrasonic wave function is capable of increasing a metabolism based on an energy vibration of about 1 million times per second for thereby implementing a good skin beauty and health.

Therefore, the total skin management system according to the present invention is directed to providing a skin with a cleansing effect and elastic force and nutrition and moisture effect based on a metabolism increase and blood circulation promotion by stimulating to a deep portion of skin by a far infrared ray, low frequency wave, ozone, low frequency vibration and ultrasonic wave for thereby making a skin young and healthier.

Figure 2:
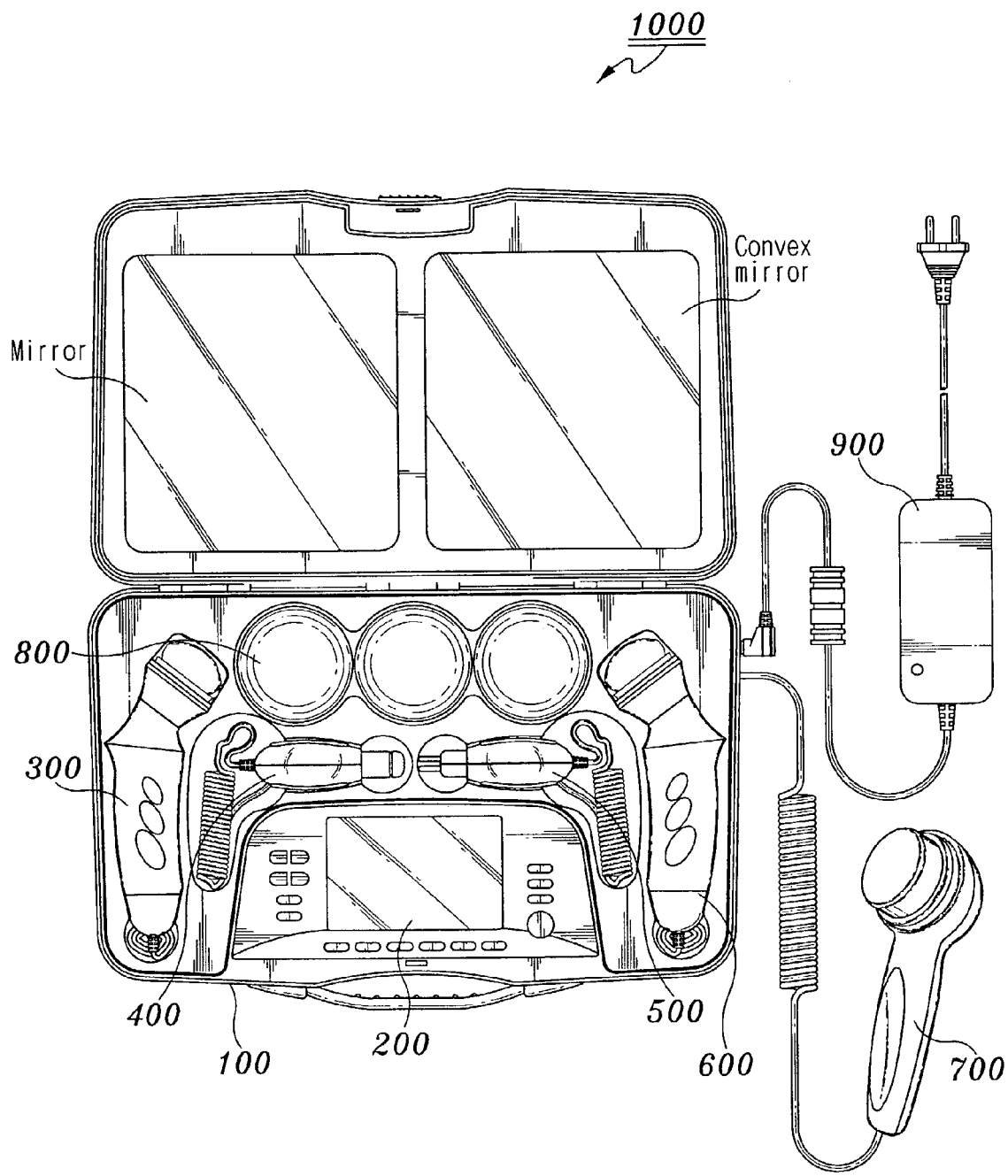
FIG. 2 is a view illustrating a state of use of a total skin management system according to a preferred embodiment of the present invention.
Figure 3:
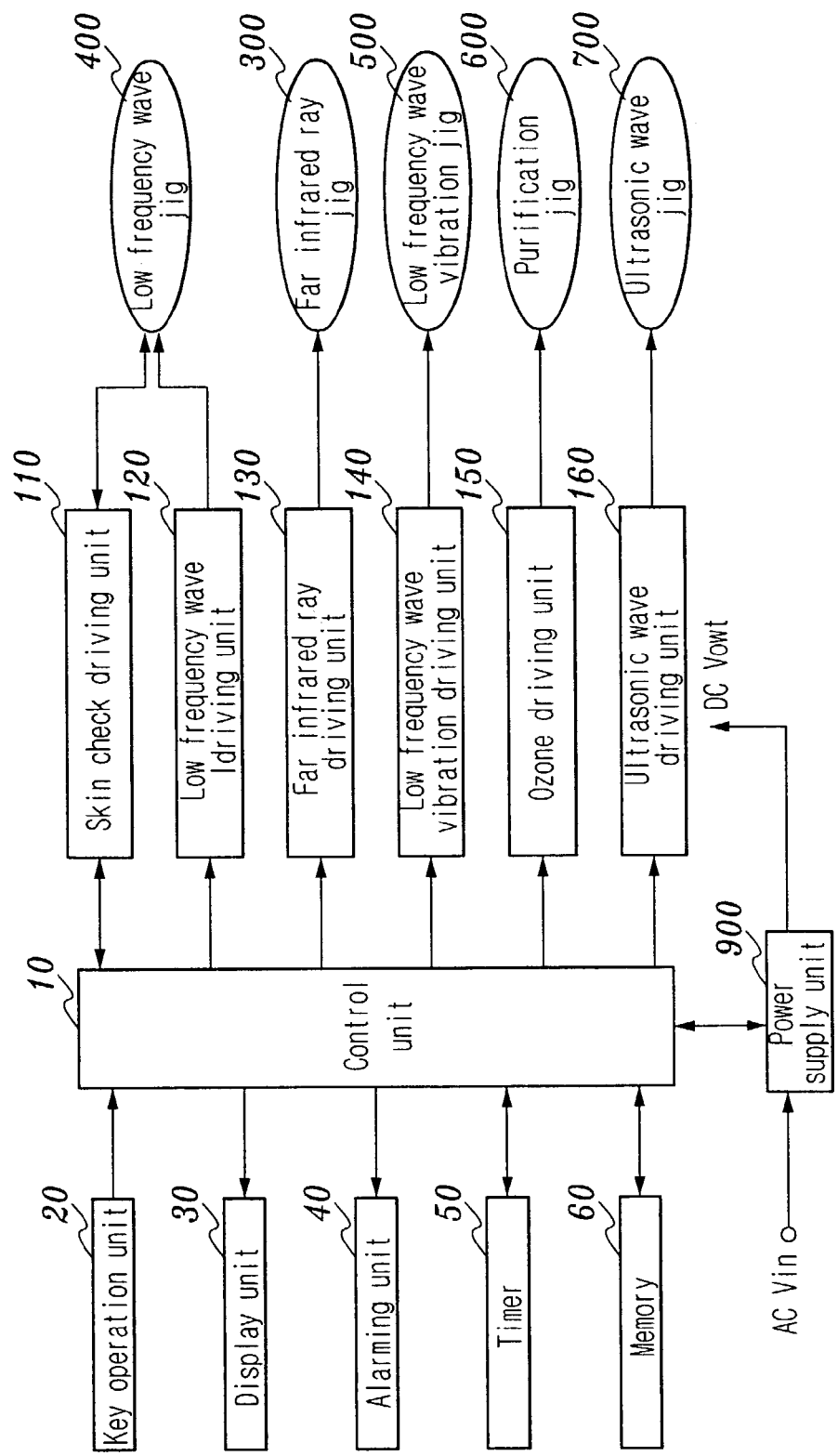
FIG. 3 is a block diagram illustrating each function unit of a total skin management system according to a preferred embodiment of the present invention.
Figure 4A:
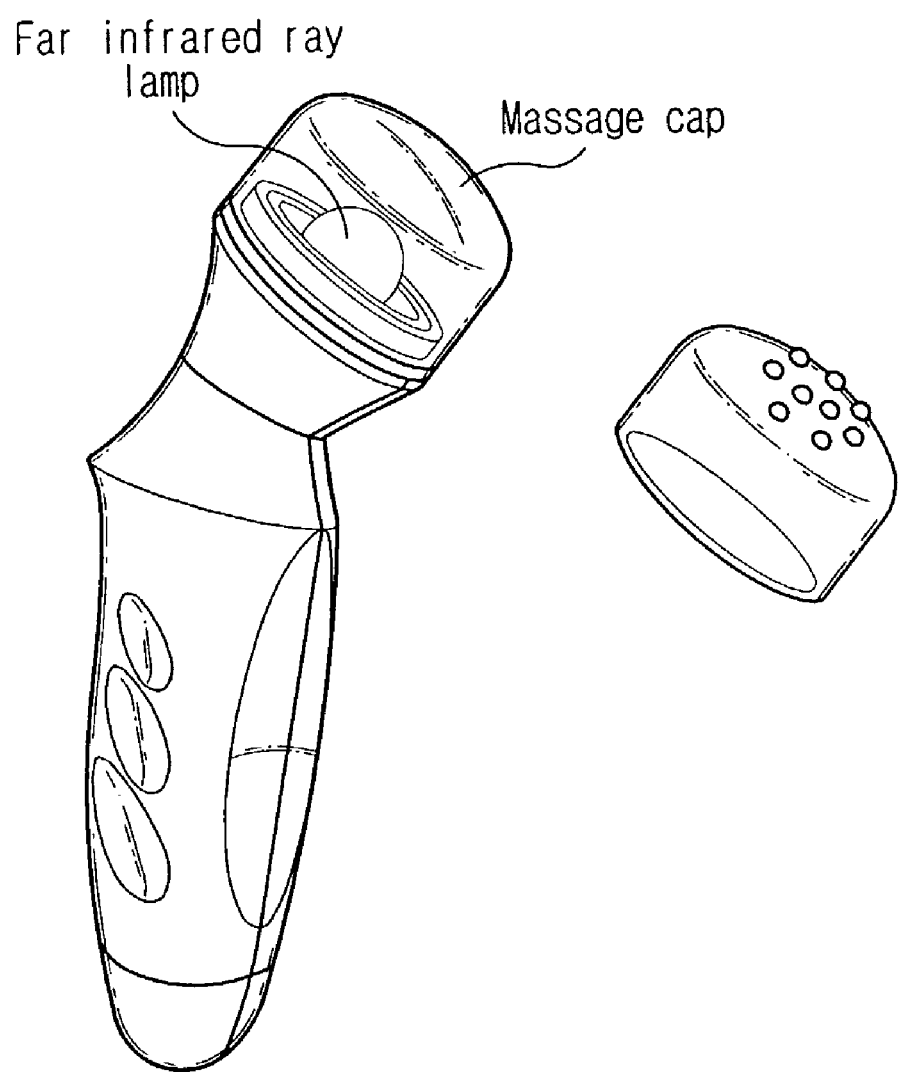
FIG. 4A is a view illustrating a far infrared ray of a total skin management system according to a preferred embodiment of the present invention.
Figure 4B:
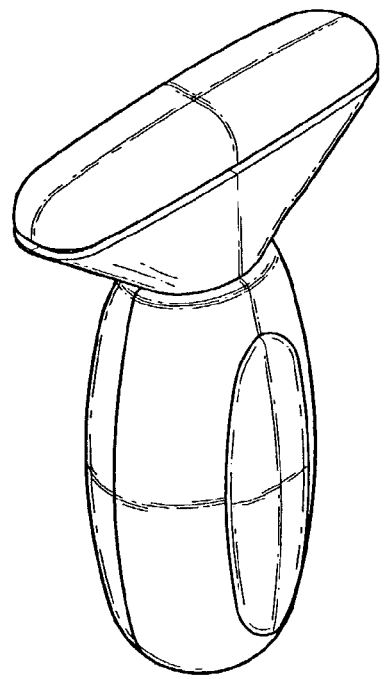
FIG. 4B is a view illustrating a low frequency wave jig of a total skin management system according to a preferred embodiment of the present invention.
Figure 4C:
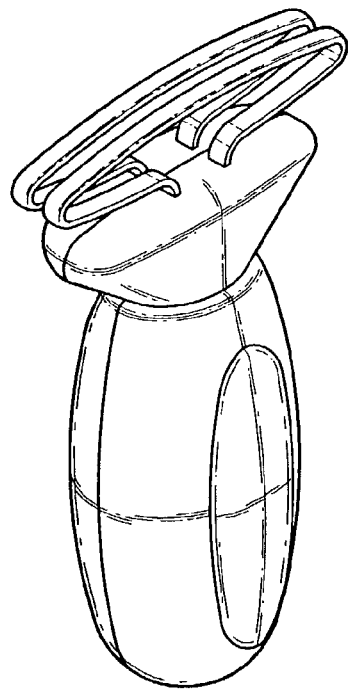
FIG. 4C is a view illustrating a low frequency vibration jig of a total skin management system according to a preferred embodiment of the present invention.
Figure 4D:
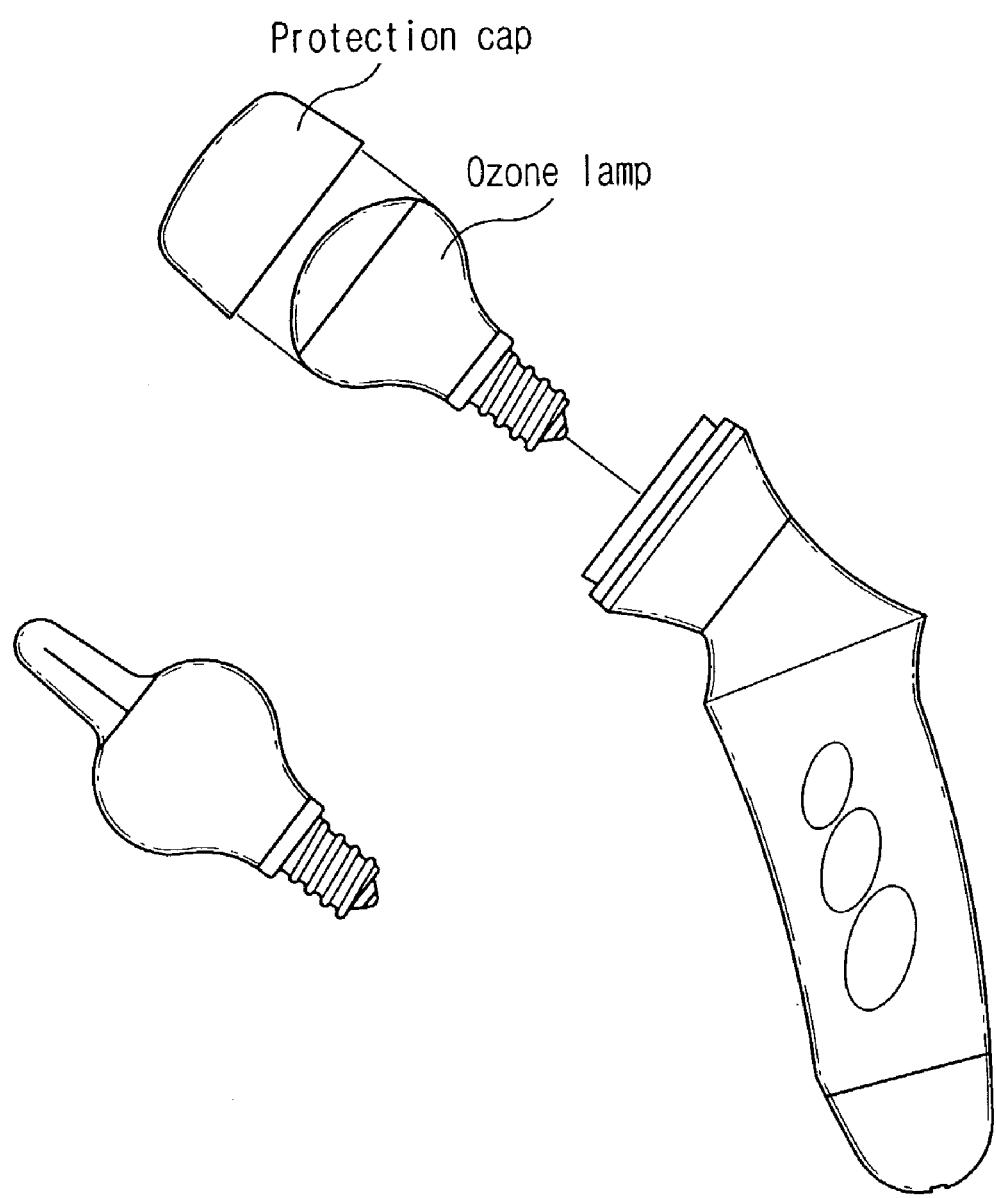
FIG. 4D is a view illustrating an ozone jig of a total skin management system according to a preferred embodiment of the present invention
Figure 4E:
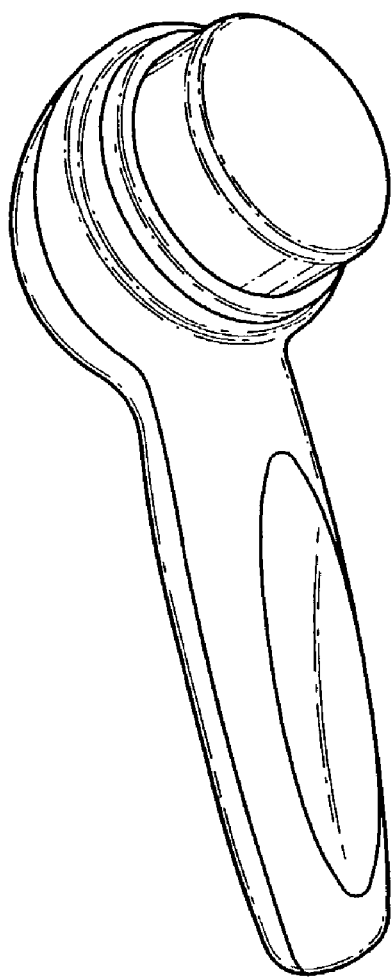
FIG. 4E is a view illustrating an ultrasonic wave jig of a total skin management system according to a preferred embodiment of the present invention.

The constructions of the total skin management system according to the present invention in order to implement the above functions are shown in FIGS. 2 through 4.

FIG. 2 is a view illustrating a state of user of a total skin management system according to a preferred embodiment of the present invention. In addition, FIG. 3 is a block diagram illustrating each function unit of a total skin management system according to a preferred embodiment of the present invention. FIGS. 4A through 4E are views illustrating various jigs for performing various functions of a total skin management system according to a preferred embodiment of the present invention.

As shown in FIG. 2, the total skin management system 1000 includes a control/display panel unit 200, various jigs, exclusive cosmetics containers and various jigs 300, 400, 500, 600 and 700 and a power supply unit 900. The total skin management system according to the present invention is capable of receiving a direct current power through the power supply unit 900 and drives various jigs connected to a corresponding connection terminal in response to a control of the control/display panel unit.

The constructions of the total skin management system according to the present invention will be described with reference to FIG. 3.

As shown in FIG. 3, the total skin management system according to the present invention includes a low frequency wave jig 400, a far infrared way jig 300, a low frequency wave vibration jig 400, a purification jig 600 and a ultrasonic wave jig 700 which are respectively connected with a control unit 10 which controls the whole elements of the system through a skin check driving unit 110, a low frequency wave driving unit 120, a far infrared ray driving unit 130, a low frequency wave vibration driving unit 140, an ozone driving unit 150 and a ultrasonic wave driving unit 160. There is further provided a power supply unit 900 which is connected with the control unit 10 for supplying a power to a display unit 30 which displays a corresponding operation, a key operation unit 20 in which various key are installed, an alarm unit 40 which generates an alarming sound, a timer 50 which counts an operation time, a memory 60 which stores a program for comprehensively managing a skin and various data for thereby supplying the power to the system.

As shown therein, the low frequency wave jig 400 is commonly connected with the skin check driving unit 110 and the low frequency wave driving unit 120 and performs a corresponding function in accordance with a control of the control unit 10. In addition, the low frequency wave driving unit 120 is controlled by the control unit 10 in response to a key input of the key operation unit 20 in order for the low frequency wave jig 400 to perform a low frequency wave(−), low frequency wave(±) and low frequency wave(+).

The construction of each element of the system will be described. The control unit 10 is formed of one chip microprocessor having a plurality of input/output terminals.

The control unit 10 performs a control operation in response to a key input from the key operation unit 20 provided in the control/display panel unit 200 provided in the body 100 of the total skin management system 1000 according to the present invention. In addition, the control unit 10 displays a key input state and a state and operation of the system in response to the key input.

The skin check driving unit 110 outputs a charge pulse for obtaining time charged up to a reference resistance value in accordance with a control of the control unit 10 in order for the control unit 10 to determine a skin type based on a reference resistance value and a skin resistance value.

The control unit 10 checks a charge voltage in accordance with a charge pulse of the skin check driving unit 100. In addition, a reference resistance is computed based on the obtained time and is stored in the memory 60. The control unit 10 checks and computes the time required until the voltage becomes a set reference voltage, through the low frequency wave jig 400.

Since the resistance value is determined based on the amount of moisture contained in skin in a state that an electrode of the low frequency wave jig 400 contacts with a skin, it is possible to measure a skin resistance based on the above manner. The control unit 10 computes the reference resistance value and skin resistance value and divides a skin type into a dry type(high, mid, low), a neutral type(high, mid, low), and an oily type(high, mid, low).

The low frequency wave driving unit 120 is connected with the control unit 10 through a connection terminal, and an output of the same is connected with the low frequency wave jig 400. The low frequency wave driving unit 120 supplies a rated power to the low frequency wave jig 400 in accordance with a control of the control unit 10.

The low frequency wave jig 400 generates a low frequency wave(−), low frequency wave(±) and a low frequency wave(+) in accordance with a control of the control unit 10.

Since the current flows from the pole(+) to the pole(−), when a low frequency wave(−) pulse voltage is applied to the skin in order for the current to flow from the inner side of the skin to the outer side of the skin, a waste material and certain toxic are discharged from the skin to the outer side of the same. Therefore, when the low frequency wave(−) function is selected, the signal(−) is applied to the pole of the low frequency wave jig 400, and the current flows to the outer side of the skin through the outer skin for thereby discharging a waste material to the outside of the skin.

On the contrary, the low frequency wave(+) function is capable of applying a signal(+) to the low frequency wave jig 400 and injecting a useful skin nutrition agent such as a bio material included in a nutrition cream from an outer skin into an inner skin, so that the skin nutrition agent is absorbed therein.

The low frequency wave(−) function is capable of alternately outputting a low frequency wave pulse every 1.5 seconds, so that the signals which affect the skin are alternately implemented. Therefore, it is possible to concurrently perform a nutrition supply function and waste material discharging function. In addition, it is possible to perform a skin massage operation without any stimulus by a weak current.

The far infrared ray driving unit 110 is connected with the control unit 10 through a connection terminal, and an output side is connected with the far infrared ray jig 300. The far infrared ray driving unit 110 is adapted to supply a rated power to the far infrared ray jig 300 in accordance with a control of the control unit 10.

A far infrared ray massage by the far infrared ray jig 300 is implemented by radiating a far infrared ray within a wavelength range of 3~50 micron, and preferably within a wavelength range of 8~14 micron, and most preferably within a microwave length range of 8~9 micron, so that the far infrared ray is penetrated into a portion under the skin by 40 mm, whereby it is possible to eliminate a waste material inside and outside the skin and prevent a formation of the waste materials.

The far infrared ray jig 300 includes a far infrared ray lamp which generates a far infrared ray for thereby generating a far infrared ray in accordance with a control of the control unit 10.

The far infrared ray jig 300 includes a massage cap having a digital compression protrusion for implementing a digital compression effect with respect to the skin. The above massage cap may be easily exchanged.

The low frequency wave vibration driving unit 140 is connected with the control unit 10 through a connection terminal and includes an output side connected to the jig 500. The low frequency wave vibration driving unit 140 is adapted to supply a rated power to the low frequency wave vibration jig 500 in accordance with a control of the control unit 10.

The low frequency wave vibration jig 500 includes a vibration device which is capable of performing a low frequency wave vibration operation in accordance with a control of the control unit 10, and a vibration member which is vibrated when the vibration device is driven and is constituted in parallel symmetrically and is adapted to perform an auxiliary switch role.

The ozone driving unit 150 is connected with the control unit 10 through a connection terminal and includes an output side connected with the purification jig 600. The ozone driving unit 150 is adapted to receive a rated power in accordance with a control of the control unit 10 and to supply a high voltage impulse for generating an ozone to the purification jig 600.

The purification jig 600 includes an ozone lamp which is capable of generating an ozone based on a pure light and is capable of transferring a high voltage impulse inputted through the ozone driving unit 150 to the ozone lamp for thereby generating an ozone based on a ultraviolet ray of a certain wavelength of 184.9 nm.

Therefore, when performing a massage operation using the purification jig 600, the generated ozone penetrates into the skin. Here, the ozone generated by the ozone lamp is adapted to implement a strong deodorization effect, skin sterilization effect, vitamin production in skin and skin whitening effect.

In addition, the sterilization by the ozone may be performed with respect to a non-scanned surface in which an ultraviolet is not scanned. As the ozone is generated by the ozone lamp, any noise does not occur in other elements, and a certain harmful element does not occur.

The ozone lamp further includes a special type ozone lamp for thereby performing a protruded portion in skin. In this case, it is possible to easily exchange the lamp.

The ultrasonic wave driving unit 160 is connected with the control unit 10 through an external connection terminal and includes an output side connected to the ultrasonic wave jig 700. The ultrasonic wave driving unit 160 is adapted to supply a rated power to the ultrasonic wave jig 700 in accordance with a control of the control unit 10.

The ultrasonic wave jig 700 includes a piezo-electric ceramic which is capable of generating a vibration about 1 million times per one second in accordance with a control of the control unit 10.

The power supply unit 900 is adapted to supply a direct current power to the total skin management system according to the present invention and is capable of supplying a rated power for driving each element in accordance with a control of the control unit 10.

The functions of each jig of the total skin management system according to the present invention will be described.

1) Low Frequency Wave Jig

As a basic skin management method, it is very important to select a certain skin management method which is proper to her/his skin after she/he knows a skin type based on an accurate skin check. The low frequency wave jig 400 is adapted to accurately classifying the skin into a dry type, neutral type, and oily type and to efficiently implement a skin management by the type of skin. In addition, the result of the skin check is classified into detailed categories, so that it is possible to perform a skin management based on an accurate function-based course.

In addition, the low frequency wave jig 400 is adapted to perform a certain exercise proper to the skin based on the low frequency wave(−), low frequency(±) and low frequency(+), so that it is possible to efficiently perform a basic massage which is most basic to the skin management from the skin cleansing to the skin nutrition. Therefore, it is possible to increase a certain elastic force to the skin through the massage exercise and to make the skin smooth.

2) Far Infrared Ray Jig

The far infrared ray jig 300 is adapted to make the skin fresh using a far infrared ray which has the same principle as a certain energy which has been traditionally used in the oriental medicine and to make a blood way of the skin clean and to discharge a waste material from the deep portion of the skin to the outside of the same for thereby implementing a healthier and elastic skin.

3) Cleansing Jig

The purification jig 600 is adapted to supply oxygen to a skin using the ozone. It is possible to implement a sterilization and cleansing effect in the skin pores, so that it is possible to make the skin clean.

4) Low Frequency Wave Vibration Jig

The low frequency wave vibration jig 500 is adapted to make the skin which may be easily damaged by a certain harmful element under a polluted environment, fresh based on a low frequency wave vibration and to exercise a skin muscle for thereby increasing a metabolism and keeping the skin young.

5) Ultrasonic Wave Jig

The ultrasonic wave jig 700 is adapted to massage a deep skin by transferring a high speed energy vibration thereto by about 1 million per second, which vibration is softly transferred to a skin. The lymph well flows in a front face based on a fine ultrasonic wave massage, and a lymph is penetrated between the cells in which a blood does not well penetrate for thereby performing a good metabolism, so that a lymph circulation and blood circulation are stimulated for thereby enhancing a skin beauty.

When a ultrasonic wave skin massage is adapted to a face skin based on a ultrasonic wave jig, a lot of micro bubbles which are formed when a ultrasonic wave passes through the skin flow in a skin surface and skin pores for thereby cleansing waste materials. In addition, a ultrasonic wave increase a temperature of a body, so that a temperature of skin is increased up to 0.5~1° C., so that a blood and lymph are stimulated, whereby a blood circulation and lymph circulation are stimulated. In addition, a skin is provided with moisture, and the skin has a certain elastic force.

In addition, when a ultrasonic wave skin massage is adapted to a body based on a ultrasonic wave jig, a fine ultrasonic wave vibration is transferred to a deep skin, so that a blood circulation is enhanced due to a slight temperature increase of a body tissue, whereby a metabolism is activated.

Since a high vibration by a ultrasonic wave is continuously transferred in a proceeding direction of a ultrasonic wave during a short period by 1 million times, in the case that a use had a surgical operation or has a heart disease, hypertension, brain infarct, skin disease and infectious disease or a user is pregnant or has a high temperature, the high vibration is not used. In addition, the high vibration is not used for eyes or teeth.

The functions and method of use and effects of a corresponding jig are shown in Table 1 for helping a understanding concerning the functions of various jigs.

In Table 1, there are shown the functions which may be performed by a manual mode among the total skin management system 1000 according to the present invention based on a certain sequence. A certain function may be performed based on the above sequence or may be selected and performed during a desired time.

The total skin management method using the total skin management system 1000 according to the present invention may be classified into a manual(selection mode) mode, an automatic mode and a fuzzy mode based on a method for performing a function-based course.

The manual mode is performed by pressing a desired function without using a start key 215 with respect to each function. The skin management is preferably performed based on the sequence shown in Table 1.

In the automatic mode, when a user knows a skin type, a certain function is selected among the functions S1, S2 and S3 based on a dry type, neutral type, oily type, pimple skin, and problem causing skin, so that the selected function is automatically performed based on the determined sequence.

TABLE 1

| Order | Function | Jigs | Cosmetics | Method | Effect |
|---|---|---|---|---|---|
| 1 | Skin check | Low frequency wave jig | None | Washing face -> water removal -> pressing skin check key -> softly contacting jig to a concave portion between lips and jaw -> standby until beep (once a month) | Accurate check for variable skin types |
| 2 | Infrared ray massage | Far infrared ray jig | Massage cream | Uniformly applying massage cream over the face -> pressing far infrared ray key -> adjusting intensity -> softly massaging from inner to outer portions in circular shape | Radiant heat of far infrared ray is penetrated into a portion below skin, obtaining a metabolism effect |
| 3 | Ozone massage | Purification jig | Massage cream | Uniformly applying massage cream over face -> pressing cleansing cream -> adjusting intensity -> softly massaging from inner to outer portions in circular shape (massage cream not used for pimple skin) (max 2 min, no time extension, only shortening) | Skin purification, skin cleansing, foreign substance removal from skin pores |
| 4 | Low frequency wave (−) massage | Low frequency wave jig | Massage cream | Uniformly applying massage cream over face -> pressing low frequency wave (−) key -> adjusting intensity -> massaging along skin pattern (lower -> upper, inner -> outer) -> wiping with steam towel after completion | Keeping clean skin, good for pimple skin, improving rough skin, enhancing a function of capillary and lymph |
| 5 | Low frequency wave jig | Low frequency wave jig | Gel cream | Uniformly applying gel cream over face -> pressing low frequency key -> adjusting intensity -> massaging along skin pattern (lower -> upper, inner -> outer) | Waste material removal from skin, keeping skin glossy and elastic |
| 6 | Low frequency wave jig | Low frequency wave jig | Nutrition cream | Uniformly applying nutrition gel cream -> pressing low frequency wave (+) key -> adjusting intensity -> massaging along skin pattern (lower -> upper, inner -> outer) | Skin protection film formation, moisture evaporation prevention, skin nutrition supply such as BIO material |
| 7 | (special management) Low frequency wave vibration jig | Low frequency wave jig | Gel cream | Uniformly applying gel cream over face -> pressing low frequency wave vibration key -> adjusting intensity -> massaging along skin pattern (lower -> upper, inner -> outer) -> wiping with towel containing warm water | Skin contraction and release operation, skin activation and skin elastic force increase |
| 8 | (special management) Ultrasonic wave jig | Ultrasonic wave jig | Ultrasonic gel cream | Applying ultrasonic wave gel -> pressing ultrasonic wave key (one time for face, two times for body) -> massaging along skin pattern (max 5 min for face, max 10 min for body, no time extension, only shortening, no intensity adjustment) | Skin cell massage, skin activation, moisture skin based on moisture supply |

In the automatic mode, when the skin type is designated after the skin is checked using the low frequency wave jig 400, the function-based course and operation time corresponding to the skin type are automatically determined. The above automatic mode may be conveniently used in the case that the user does not know the skin type-based management and when the user wishes to perform the skin type-based management more conveniently.

After a certain course corresponding the skin type is selected, when the start key is pressed, the function-based operation time are automatically set and displayed on the LCD screen as shown in Table 2, and the system becomes the standby mode.

TABLE 2

| Skin type | Pressed Number of automatic key | Course | Far infrared ray massage | Ozone massage | Low frequency wave (−) massage | Low frequency wave (±) massage | Low frequency wave (+) massage |
|---|---|---|---|---|---|---|---|
| Dry | 1 time | S1 | 4 min | 1 min | Omitted | | 4 min |
| Neutral | 2 times | S2 | 4 min | 1 min 30 sec | 2 min 30 sec | | 2 min 30 sec |
| Oily | 3 times | S3 | 4 min | 2 min | 4 min | | Omitted |

The course is performed in the sequence of far infrared ray->purification->low frequency wave(−)->low frequency wave(±)->low frequency wave(+), and the face washing and jig and cosmetics which will be used are automatically designated for a corresponding sequence based on each function. The thusly designated contents are displayed on the LCD screen.

The fuzzy mode is directed to a mode that the function-based operation time and sequence are automatically performed with a program based on a result of the skin check.

The fuzzy mode is directed to a course that the function-based course and operation time are automatically performed with a fuzzy program stored in a memory of the total skin management system according to the present invention after the state of the skin is checked.

In the fuzzy mode, the skin is checked by slightly pressing the low frequency wave jig 400 at a portion between the lips and jaw. When the skin check is complemented, the jig which will be used and the function-based course and proceeding time are automatically designated based on the type of the skin.

At this time, a certain course may be omitted based on the state of the skin or the operation time may be extended or shortened. Table 3 shows the function-based course and each function-based operation time based on a result of the skin check in the fuzzy mode.

display unit based on the type of skin, a skin check value display unit, a remaining time display unit, a weak/mid/strong operation intensity graph display unit, a skin check result graph display unit, a cosmetics-used display unit, a standby/operation mode display unit, a ultrasonic wave massage in-operation display unit, a ultrasonic wave massage portion selection display unit and jig-used display unit.

The skin check unit 201 is selected for checking skin. In this case, the low frequency wave jig 400 is displayed on the SCD screen of the display unit 30. When checking the skin through the low frequency wave jig 400, the skin check value and skin type are displayed in graphic.

The far infrared ray key 203 is selected for using a far infrared ray function. When the far infrared ray key 203 is selected, the far infrared ray jig 300 is displayed on the SCD screen of the display unit 30. When the far infrared ray function is performed through the far infrared ray jig 300, the function-based operation time, operation intensity and cosmetics which will be used, are displayed.

The purification key 205, the low frequency wave(−) key 207, the low frequency wave(±) key 209, the low frequency wave(+) key, and the low frequency vibration key 213 are performed for a purification function, low frequency wave (−) function, low frequency wave(±) function, low frequency wave(+) function and low frequency wave vibration function, respectively.

TABLE 3

| | | | Massage time | | |
|---|---|---|---|---|---|
| Result of skin check (skin type) | Far infrared ray | purification | Low frequency wave (−) | Low frequency wave (±) | Low frequency wave (+) |
| Dry 1 | 4 min | 1 min | Omitted | 4 min | 4 min 30 sec |
| Dry 2 | 4 min | 1 min | Omitted | 4 min | 4 min |
| Dry 3 | 4 min | 1 min | Omitted | 4 min | 3 min 30 sec |
| Neutral 1 | 4 min | 1 min 30 sec | 2 min | 4 min | 3 min |
| Neutral 2 | 4 min | 1 min 30 sec | 2 min 30 sec | 4 min | 2 min 30 sec |
| Neutral 3 | 4 min | 1 min 30 sec | 3 min | 4 min | 2 min |
| Oily 1 | 4 min | 2 min | 3 min 30 sec | 4 min | Omitted |
| Oily 2 | 4 min | 2 min | 4 min | 4 min | Omitted |
| Oily 3 | 4 min | 2 min | 4 min | 4 min | Omitted |

As described above, the total skin management method according to the present invention will be described with reference to FIGS. 5 through 8.

FIG. 1 is a view illustrating a control/display panel unit for comprehensively controlling a total skin management system according to a preferred embodiment of the present invention. As shown therein, the operation is performed in response to various key inputs by a user for a total skin management according to the present invention, and an information thereon is displayed.

Figure 5:
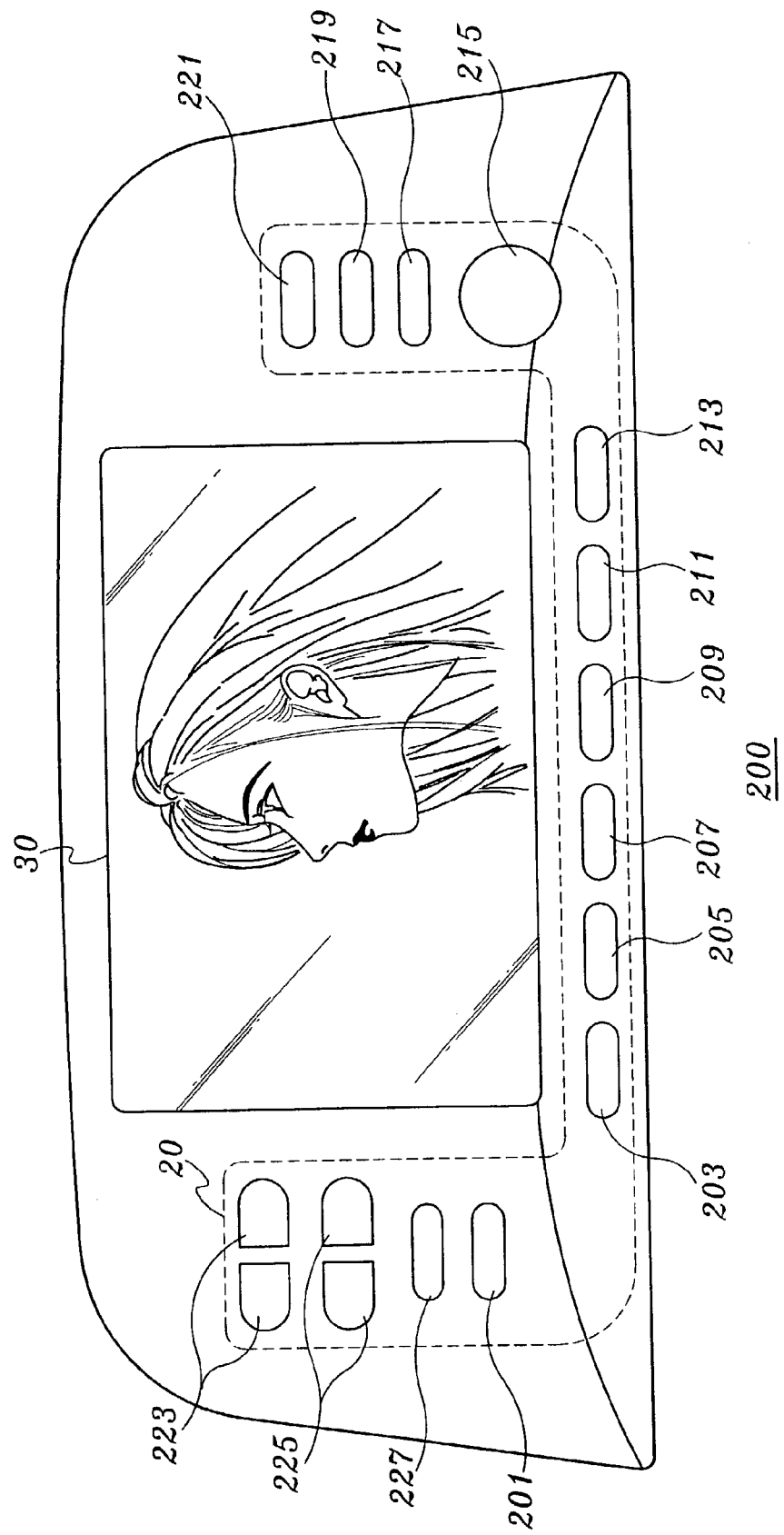
FIG. 5 is a view illustrating a control/display panel unit of a total skin management system according to a preferred embodiment of the present invention.

As shown in FIG. 5, the control/display panel unit 200 includes a key operation unit 20, and a display unit 30. The key operation unit 20 includes a skin check key 201, a far infrared ray key 203, a purification key 205, a low frequency wave(−) key 207, a low frequency wave(±) key 209, a low frequency wave(+) key 211, a low frequency wave vibration key 213, a start key 215, a ultrasonic wave key 217, an automatic key 219, a fuzzy key 221, an intensity adjusting key 223, a time adjusting key 225, and a temporary stop/cancel key 227.

The display unit 30 is implemented by a LCD (Liquid Crystal Display) panel and is formed of a manual/automatic/intelligence mode display unit, a S1/S2/S3 course selection In addition, a function corresponding to a key detected when a key is selected is performed, and the function-based operation time, operation intensity, and jig and cosmetics which will be used, are displayed.

The start key 215 is selected when the fuzzy function is started.

The ultrasonic wave key 217 is selected when the ultrasonic wave function is started in the case that it is needed an effect for increasing a skin activity based on a blood circulation increase.

The automatic key 219 is selected for selecting her/his own skin type and automatically setting a function corresponding to the selected skin type.

The fuzzy key 221 is selected for automatically recognizing a result obtained based on a user's skin check and type and automatically setting a function proper thereto.

The intensity adjusting key 223 is selected for adjusting the intensity of each function based on weak/mid/strong, namely, step 1, step 2, and step 3.

The time adjusting key 225 is selected for shortening or extending a corresponding function operation time by 30 seconds for one time input.

When the temporary stop/cancel key 227 is pressed one time, the system stops, and when the same is pressed two times, the current operation is ended.

Figure 6:
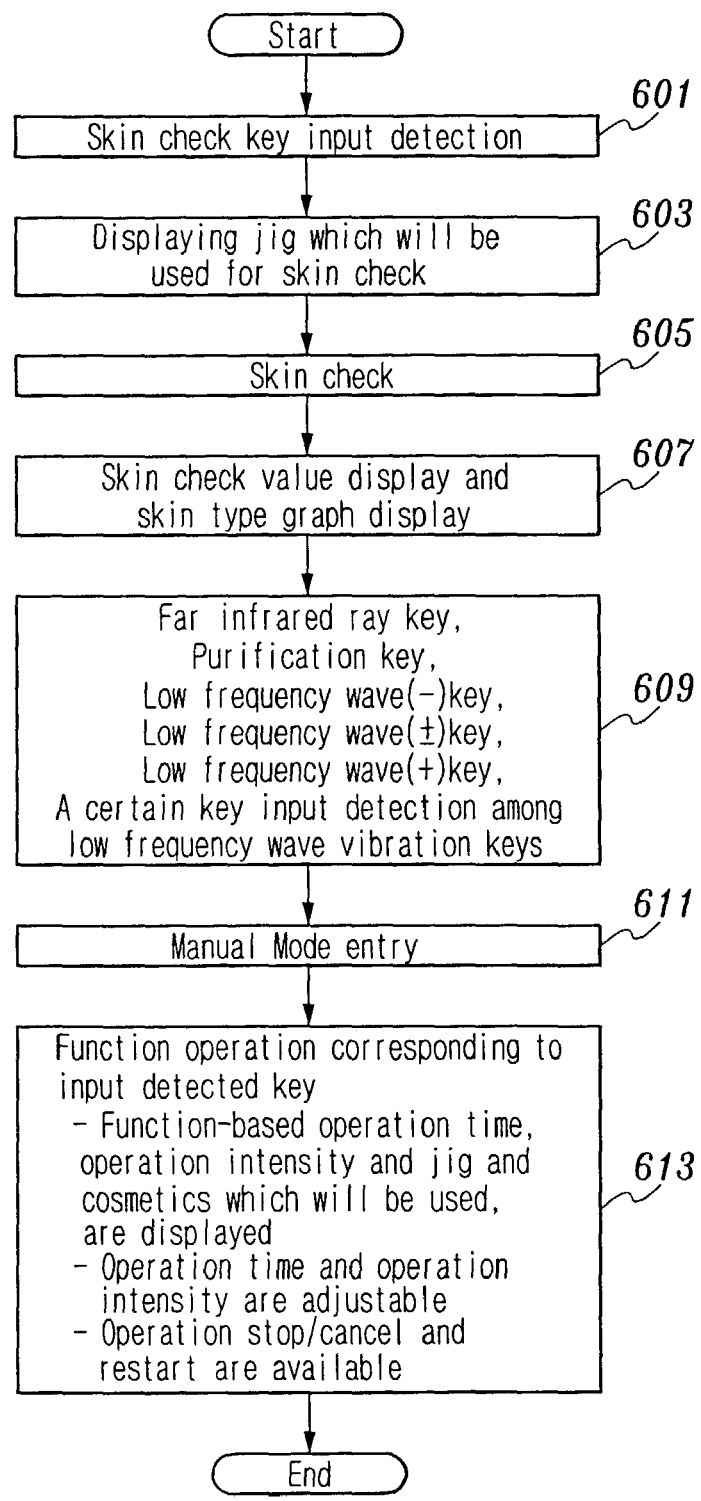
FIG. 6 is a flow chart illustrating a method for performing a total skin management in a manual mode using a total skin management system according to a preferred embodiment of the present invention.
Figure 7:
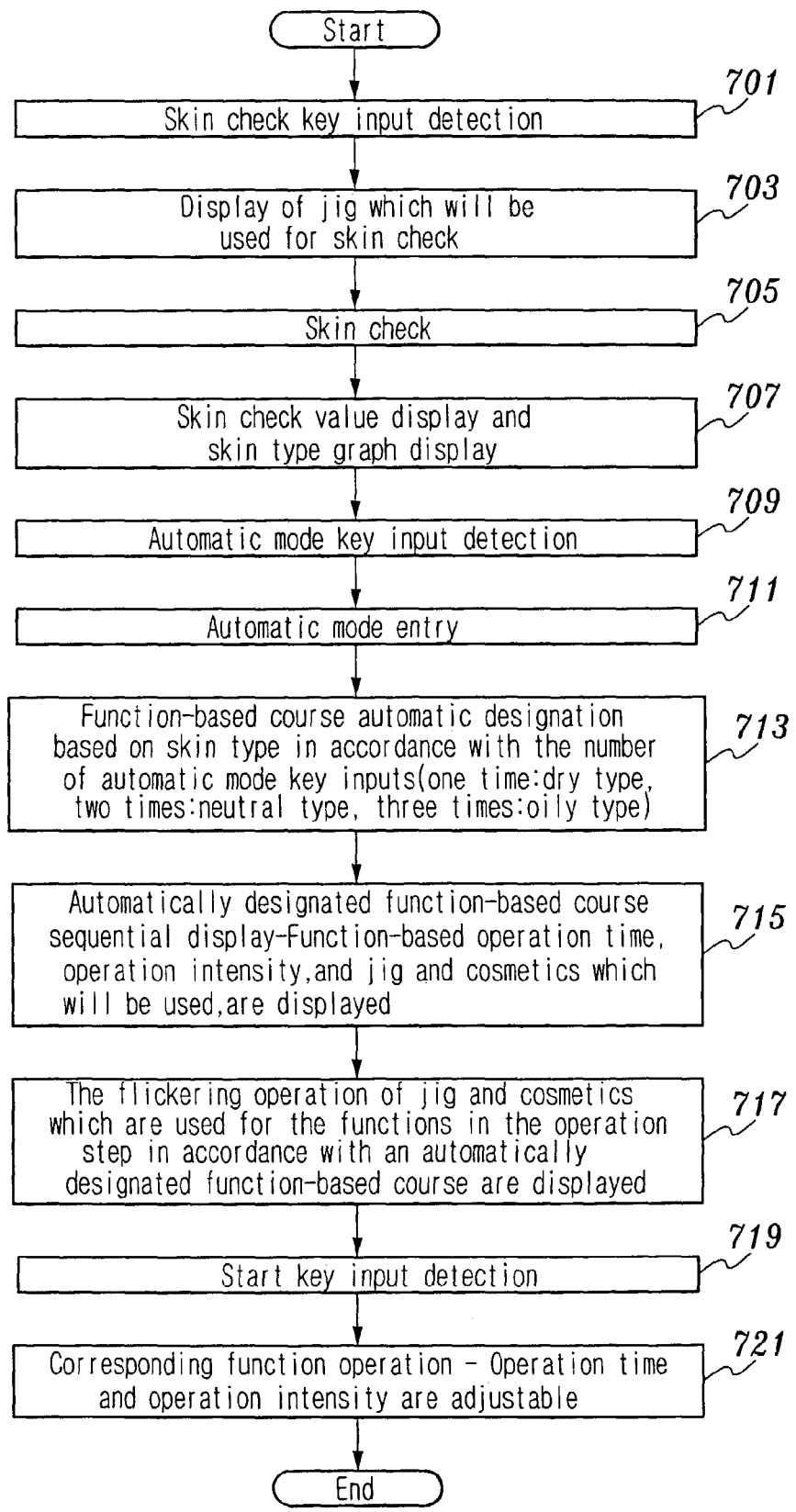
FIG. 7 is a flow chart of a method for performing an automatic mode using a total skin management system according to a preferred embodiment of the present invention.
Figure 8:
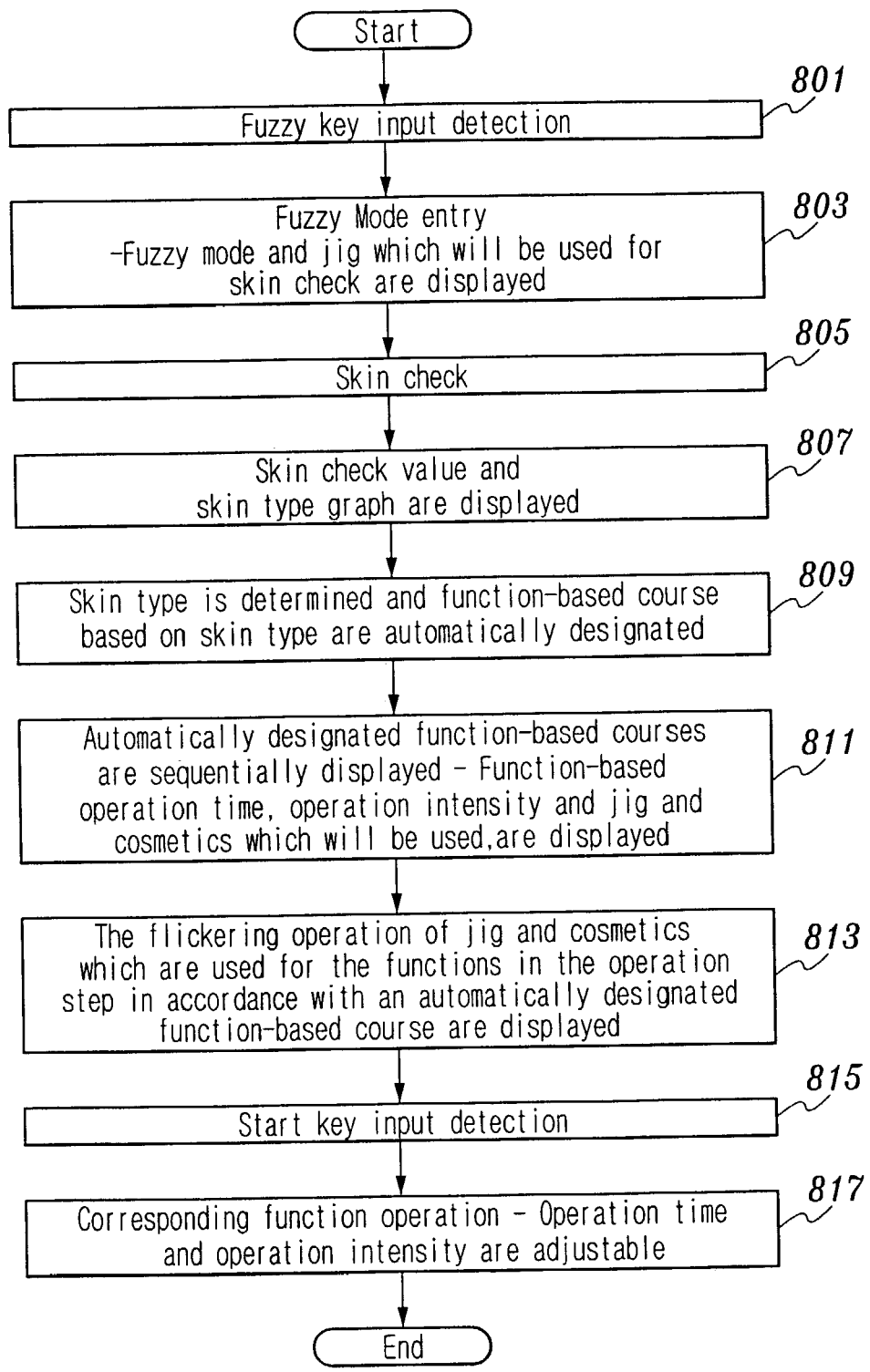
FIG. 8 is a flow chart of a method for performing a total skin management in a fuzzy mode using a total skin management system according to a preferred embodiment of the present invention.

FIGS. 6 through 8 are flow charts illustrating a method for performing a total skin management based on the manual mode, automatic mode and fuzzy mode using the total skin management system according to a preferred embodiment of the present invention.

The manual mode performing method according to a preferred embodiment of the present invention will be described with reference to FIG. 6.

As shown in FIG. 6, when the control unit 10 of FIG. 3 detects an input of the skin check key 201 which is inputted externally in Step 601, the current routine goes to Step 603. In Step 603, the jig which will be used for checking the skin is displayed on the LCD panel of the display unit 30. Therefore, when a user checks the skin using the displayed jig(lower frequency wave jig when checking skin), the control unit 10 receives a skin check data from the low frequency wave jig 400 and computes a result of the skin check.

In addition, the control unit 10 performs Step 607 and displays a skin check value and graph obtained as a result of the skin check at a certain portion of the LCD panel of the display unit 30.

When the user inputs a certain key among the far infrared ray key 203, the purification key 205, the low frequency wave(−) key 207, the low frequency wave(±) key 209, the low frequency wave(+) key 211, the low frequency wave vibration key 213 and the ultrasonic wave key 217 based on the checked type of the skin, in Step S609, the inputted information is detected, and the routine goes to Step S611. In Step S611, a corresponding function is performed based on the inputted key.

The control unit 10 performs a corresponding function based on an inputted key without an input of the start key 215 and displays a function-based operation time, operation intensity, and jig and cosmetics which will be used, are display at a certain portion of the LCD panel of the display unit 30 in character and graphic. Table 1 shows the function-based jigs which will be used, the cosmetics used, the method of use and the effects.

At this time, when The inputs of the time adjusting key 225 and intensity adjusting key 223 are detected, the control unit 10 adjusts the operation time and operation intensity of a function which is currently performed. In addition, when there is an input of the operation stop/cancel key 227, the control unit 10 temporarily stops and cancels a function which is currently performed, and the stopped function is restarted based on an input of the start key 215.

In addition, even when an input of the time adjusting key 225 by the user is inputted while the purification function among various functions is being performed, in the case that the purification function is over used, the control unit 10 controls in order for the massage time not to exceed 2 minutes in maximum because the over use of the same may damage the skin.

Next, the automatic mode performing method according to a preferred embodiment of the present invention will be described with reference to FIG. 7.

In Step S701 of FIG. 7, when the control unit 10 of FIG. 3 detects an input of the skin check key 201 which is inputted externally, the routine goes to Step S703, and the control unit 10 displays the jig which will be used for checking the skin, on the LCD panel. When a user checks the skin using the displayed jig (low frequency wave jig when checking skin), the control unit 10 receives a skin check data from the low frequency wave jig 400 and computes a result of the skin check in Step S705.

In addition, the routine goes to Step S707, and the control unit 10 displays a skin check value and graph obtained based on a result of the skin check, at a certain portion of the LCD panel of the display unit 30.

When the control unit 10 detects an input of the automatic key 219 of the user in Step S709, the routine goes to Step S711, and the automatic mode is performed.

In Step S713, the control unit 10 detects an input of the automatic key 219 inputted by the user and automatically designates the function-based course corresponding to the type of the skin based on the number of inputs. Table 2 shows the skin types and function-based courses based on the number of the key inputs. When the automatic key 219 is inputted one time, the dry type of skin is designated, and when the same is inputted two times, the neutral type of skin is designated, and when the oily type of skin is inputted three times, the function-based course corresponding to the oily skin is designated.

Thereafter, the control unit 10 sequentially displays the function-based courses which are automatically designated and displays the function-based operation time, operation intensity and jig and cosmetics which will be used, at a certain portion of the LCD panel of the display unit 30.

In Step S717, the control unit 10 flickers the portions of the jig and cosmetics which will be used for the functions of the operation steps based on the automatically designated function-based courses for thereby indicating the currently standby functions.

In Step S719, the control unit 10 controls the constructions for thereby detecting an input of the start key 215, and the routine goes to Step S721 for thereby controlling the constructions so that a corresponding function is performed.

A this time, when an input of the time adjusting key 225 or the intensity adjusting key 223 of the user is inputted, the control unit 10 adjusts the operation time or operation intensity of the function which is currently performed. In addition, when there is an input of the operation stop/cancel key 227, the control unit 10 temporarily stops and cancels the function which is currently performed, and the temporarily stopped function is restarted based on an input of the start key 215.

Finally, the fuzzy mode performing method according to a preferred embodiment of the present invention will be described with reference to FIG. 8.

In Step S801 of FIG. 8, in the control unit 10, when an input of the user's fuzzy key 221 is detected, the routine goes to Step S803, and the intelligence mode is started.

As the user's fuzzy key 221 is inputted, the control unit 10 displays the fuzzy mode and the jig which will be used for checking the skin in Step S803.

When the fuzzy mode is set, the routine goes to Step S805, and the control unit 10 displays the jig which will be used for checking the skin, on the LCD panel of the display unit 30. When the user checks the skin using the jig(low frequency wave jig when checking the skin) displayed, the control unit 10 receives a skin check data from the low frequency wave jig 400 and computes a result of the skin check.

In addition, in Step S807, the control unit 10 displays a skin check value and graph which are obtained as a result of the skin check, at a certain portion of the LCD panel of the display unit 30. In Step S809, the control unit 10 automatically designates the function-based course based on the determined skin type, and in Step S811, the control unit 10 sequentially displays the automatically designated function-based course, and the user is informed by displaying the function-based operation time, operation intensity, and the jig and cosmetics which will be used, at a certain portion of the LCD panel of the display unit 30 in character and graphic.

Table 3 shows the function-based courses and function-based operation time which are automatically designated in accordance with the skin type in the fuzzy mode.

In Step S813, the control unit flickers the portions corresponding to the jig and cosmetics which will be used for a corresponding function in the operation step in accordance with the automatically designated function-based course for thereby indicating the function which is in the standby mode.

Thereafter, in Step S815, the control unit 10 detects an input of the start key 215, and the routine goes to Step S817, and the control unit 10 controls the constructions for thereby performing a corresponding function.

At this time, when an input of the user's time adjusting key 225 or intensity adjusting key 223 is detected, the control unit 10 adjusts the operation time or operation intensity of the current function. In addition, when there is an input of the operation stop/cancel key 227, the control unit 10 temporarily stops and cancels the current function and restarts the temporarily stopped function in accordance with an input of the start key 215.

Figure 9:
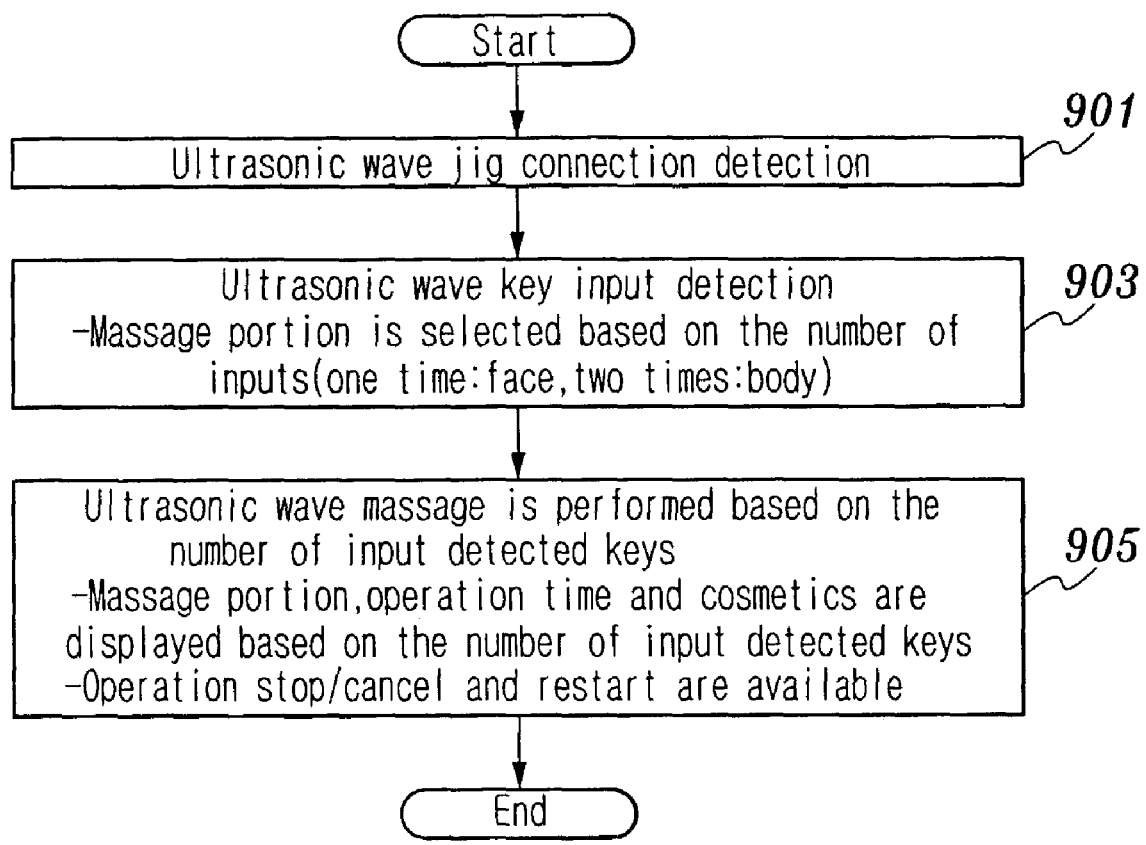
FIG. 9 is a view illustrating a method for performing a ultrasonic wave massage of a total skin management system according to a preferred embodiment of the present invention.

FIG. 9 is a flow chart of a method for performing a ultrasonic wave massage of a total skin management system according to a preferred embodiment of the present invention. As shown therein, the control unit 10 of FIG. 3 detects a connection state of the ultrasonic wave jig 700.

When the ultrasonic wave jig 700 is connected, the control unit 10 selects a massage portion based on the number of inputs of the user's ultrasonic wave key 217 in Step S903 and displays the selected portion at a certain portion of the LCD panel of the display unit 30.

When the ultrasonic wave key 217 is inputted one time, the control unit 10 displays the massage portion, operation time and cosmetics which will be used, so that the routine goes to Step S905, and a face portion is massaged, and a corresponding ultrasonic wave massage is performed. In addition, When the ultrasonic wave key 217 is inputted two times, the control unit 10 displays the massage portion, operation time and cosmetics which will be used, so that a corresponding ultrasonic wave massage is performed, and the body portion is performed based on the ultrasonic wave massage in Step S905.

At this time, when an input of the user's time adjusting key 225 or intensity adjusting key 223 is detected, the control unit 10 adjusts the operation time or operation intensity of the current function. In addition, in the case that the ultrasonic wave massage function is over used, since the skin may be damaged, the control unit 10 controls in order for the massage time not to exceed max 5 minutes for the face and not to exceed max 10 for the body in,the case that the user's time adjusting key 225 and intensity adjusting key 223 are inputted for thereby adjusting the time and intensity. In addition, the control unit 10 controls in order for the operation intensity not to exceed a set intensity.

In addition, when there is an input of the operation stop/cancel key 227, the control unit 10 temporarily stops and cancels the current function and restarts the temporarily stopped function in accordance with an input of the start key 215.

The total skin management method which is implemented based on the manual mode, automatic mode and fuzzy mode of the total skin management system according to the present invention will be described by dividing the functions into implementation possible functions.

1) Skin State Check Step

A user's face is cleanly washed, and water is fully eliminated, and then the skin check key is pressed. The state of the skin is accurately checked using the low frequency wave jig for thereby classifying the state of the skin into the dry type, neutral type and oily type, so that the data are obtained for setting the operation time, operation intensity and function-based course of each mode.

2) Skin Cleansing Step

A massage cream is uniformly applied over a face, and then the far infrared ray key is pressed. The operation time and operation intensity are adjusted in accordance with the type of skin. The skin is massaged from an inner portion to an outer portion in a circle shape.

When the selected operation time(for example, 4 minutes) is passed, and an alarming sound is generated, the massage cream is cleanly wiped away using a water towel. Thereafter, the massage cream is uniformly applied over the face, and then the purification key is pressed. The operation time and operation intensity are adjusted based on the type of skin. The massage is smoothly performed from an inner portion to an outer portion in a circle shape.

When the selected operation time(for example, 2 minutes) is passed, if an alarm is generated, the cream is wiped away using a water towel. Thereafter, the massage cream is uniformly applied over the face again, and the low frequency wave(−) key is pressed. The operation time and operation intensity are adjusted based on the type of skin. The massage is performed from a lower portion to an upper portion and from an inner portion to an outer portion, forming a circle. As the operation time is passed, when the alarm sound is outputted, the cream is wiped is away by a steam towel.

(3) Skin Beauty Step

A gel cream is uniformly applied over the face, and the low frequency wave(±) key is pressed. The operation time and operation intensity are adjusted based on the type of skin. The massage is performed from a lower portion to an upper portion and from an inner potion to an outer portion, forming a circle along a skin pattern. As the operation time is passed, when an alarming sound is outputted, the cream is wiped away using a water towel.

(4) Skin Nutrition Supply Step

The nutrition cream is uniformly applied over the face again, and the low frequency wave(+) key is pressed. The operation time and operation intensity are adjusted based on the type of skin. The massage is performed from a lower portion to an upper portion and from an inner portion to an outer portion along a skin pattern. As the operation time is passed, when an alarming sound is outputted, the face is just touched by a tissue or the face remains as it is.

(5) Special Skin Management Step

A gel cream is uniformly applied over the face. The low frequency wave vibration key is pressed. The operation time and operation intensity are adjusted based on the type of the skin. The massage is performed from a lower portion to an upper portion and from an inner portion to an outer portion. As the operation time is passed, when an alarming sound is outputted, the cream is wiped away using a towel containing warm water.

A ultrasonic wave gel is uniformly applied over the face. The ultrasonic wave key is pressed. Thereafter, the massage is performed along a kin pattern.

According to the management of the skin using the total skin management system according to the present invention, it is possible for the user to easily check the type of skin based on the check of the skin. Therefore, the operation time and operation intensity are properly adjusted in the skin management steps using the skin cleansing, skin beauty, skin nutrition, low frequency wave vibration and ultrasonic wave based on the checked type of skin, so that it is possible to comprehensively perform a skin management at home.

In the total skin management system and the total skin management method using the same according to the present invention, the type of skin is known by checking the skin, and the function-based courses are manually or automatically performed for a total skin management based on the checked type of skin. In addition, a person who is not skilled in the field of skin beauty is capable of easily performing the total skin management based on the check of the skin. Various functions for totally managing the skin are integrated in one chip processor, so that it is possible to totally manage the skin based on a controllable portable system, whereby a professional skin management is implemented at a lower cost at any time.

As described above, in the present invention, it is possible to accurately check the type of skin, and the total skin management method is prepared based on the checked type of skin, so that a certain person can accurately check the type of skin and implement a total skin management based on her/his own skin type. In the present invention, a certain person can easily adjust a desired skin management function based on various modes with respect to her/his own skin type, and it is possible to properly combine the total skin management functions.

Furthermore, the present invention is basically directed to implement a portable combined system which is capable of integrating and controlling various total skin management functions such as a skin check, far infrared ray massage, ozone massage, low frequency wave massage, low frequency wave vibration massage and ultrasonic wave massage, so that it is possible to totally manage the skin based on her/his own skin type at any time.

As the present invention may be embodied in several forms without departing from the spirit or essential characteristics thereof, it should also be understood that the above-described examples are not limited by any of the details of the foregoing description, unless otherwise specified, but rather should be construed broadly within its spirit and scope as defined in the appended claims, and therefore all changes and modifications that fall within the meets and bounds of the claims, or equivalences of such meets and bounds are therefore intended to be embraced by the appended claims.

What is claimed is:

1. In a system for comprehensively managing a skin, a total skin management system, comprising:
    a low frequency wave jig which outputs a charge pulse for a skin check and a low frequency wave pulse for a low frequency wave massage;
    a far infrared ray jig which outputs a far infrared ray by providing a far infrared ray lamp which is capable of outputting a far infrared ray;
    a low frequency wave vibration jig which is formed of a vibration device for performing a low frequency wave vibration operation, and a vibration member which vibrates when the vibration device is driven based on a voltage inputted, wherein said vibration member comprises at least two symmetrically shaped elements positioned in parallel with one another and operates as an auxiliary switch;
    a purification jig which includes an ozone lamp for generating an ozone based on light and is capable of transferring a high voltage impulse to the ozone lamp and generating an ozone based on a ultraviolet ray of a certain wavelength;
    a ultrasonic wave jig which includes a piezo-electric ceramic member for generating a vibration based on an input voltage and outputs a ultrasonic wave vibration;
    a skin check driving unit which outputs a charge pulse for a reference resistance value through the low frequency wave jig for obtaining a reference resistance value and skin resistance value which are a basis to determine the type of skin;
    a low frequency wave driving unit which is connected with a control unit through a connection terminal and includes an output terminal connected with the low frequency wave jig for thereby supplying a rated power to the low frequency wave jig;
    a far infrared ray driving unit which is connected with the control unit through a connection terminal and is connected with the far infrared ray jig for thereby supplying a rated power to the far infrared ray jig;
    a low frequency wave vibration driving unit which is connected with the control unit through a connection terminal and is connected with the low frequency wave vibration jig for thereby supplying a rated power to the jig;
    an ozone driving unit which is connected with the control unit through a connection terminal and has an output terminal connected with the purification jig for thereby receiving a rated power and supplies a high voltage impulse for generating an ozone to the purification jig;
    a ultrasonic wave driving unit which is connected with the control unit through an external connection terminal and has an output terminal connected with the ultrasonic wave jig for thereby supplying a rated power to the ultrasonic wave jig;
    a key operation unit which includes various control keys and receives a user's key input signal;
    a display unit which displays a corresponding operation corresponding to a key input of the key operation unit;
    a memory which stores a program for a total skin management and various data;
    a control unit which is formed of one chip microprocessor having a plurality of input/output terminals and performs a control operation in response to a key input from the key operation unit and displays a key input and a state and operation of the system based on the key input on the display unit and comprehensively controls the system; and
    a power supply unit which receives an alternating current power and supplies a rated direct current to the system and supplies a rated direct power for driving each element in accordance with a control of the control unit.

2. The system of claim 1, wherein said key operation unit includes a skin check key, far infrared ray key, purification key, low frequency wave(−) key, low frequency wave(□) key, low frequency wave(+) key, low frequency wave vibration key, start key, ultrasonic wave key, automatic key, fuzzy key, time adjusting key and temporary stop/cancel key.

3. The system of claim 1, wherein said display unit includes a LCD panel which is formed of an automatic/manual/fuzzy mode display unit, S1/S2/S3 course selection display unit based on a skin type, skin check value display unit, remaining time display unit, weak/mid/strong operation intensity graph display unit, skin check result graph display unit, cosmetics display unit, standby/operation mode display unit, ultrasonic wave massage in-operation display unit, ultrasonic wave massage portion selection display unit and jig-used display unit.

4. The system of claim 1, wherein said low frequency wave driving unit includes a plurality of functions capable of outputting a low frequency wave (−), low frequency wave (□) and low frequency wave(+) to the low frequency wave jig, respectively, in accordance with a control of the control unit with respect to a key input of the key operation unit.

5. The system of claim 1, wherein said control unit is adapted to compute a reference resistance value of the low frequency wave jig and a skin resistance value determined based on the amount of moisture in a state that a pole of the low frequency wave jig is contacted with the skin and classify the type of skin into nine classes formed of a dry type(low, mid, high), neutral type(low, mid, high), and oily type(low, mid, high).

6. The system of claim 1, wherein said far infrared ray jig further includes a massage cap having a digital compression protrusion for thereby implementing a digital compression effect with respect to the skin.

7. The system of claim 1, wherein said purification jig further includes an ozone lamp which has a special construction for thereby conveniently massaging a protruded portion of the skin.

8. The system of claim 1, further comprising:
an alarming unit which outputs an alarming sound when a corresponding function is changed or a certain function of the system is ended.

9. The system of claim 1, further comprising:
a timer which is capable of counting an operation time of a corresponding function.

10. In a method for comprehensively managing a skin using a total skin management system, a total skin management method, comprising:
a skin state check step in which a face is cleanly washed, water is wiped away from the face, a skin check key is pressed, the type of the skin is classified into a dry type, neutral type, oily type using the low frequency wave jig, and a data is obtained for setting an operation time and operation intensity and function-based course of each mode;
a skin cleansing step in which a massage cream is uniformly applied over a face, a far infrared key is pressed, an operation time and operation intensity are adjusted based on the type of skin, the massage is smoothly performed from an inner portion to an outer portion, forming a circle, and when a selected operation time is passed, and an alarming sound is outputted, the cream is wiped out, and then the massage cream is uniformly applied over the face again, the purification key is pressed, the operation time and operation intensity are adjusted based on the type of skin, the massage is smoothly performed from an inner portion to an outer portion, forming a circle, and when a selected time is passed, and an alarming sound is outputted, the cream is wiped away using a water towel, and then the massage cream is uniformly applied over a whole portion of the face again, the low frequency wave key is pressed, the operation time and operation intensity are adjusted based on the type of skin, the massage is performed from a lower portion to an upper portion and from an inner portion to an outer portion along a skin pattern, and when the operation time is passed, and an alarming sound is outputted, the cream is wiped away using a steam towel;
a skin beauty step in which a gel cream is uniformly applied over the face, a low frequency wave(□) key is pressed, an operation time and operation intensity are adjusted based on the type of skin, the massage is performed from a lower portion to an upper portion and from an inner portion to an outer portion along a skin pattern, and when the operation time is passed and an alarming sound is outputted, the cream is wiped away using a water towel;
a skin beauty nutrition supply step in which a nutrition cream is uniformly applied over the face, a low frequency wave(+) key is pressed, an operation time and operation intensity are adjusted based on the type of skin, the massage is performed from a lower portion to an upper portion and from an inner portion to an outer portion along a skin pattern, and when the operation time is passed and an alarming sound is outputted, the cream is wiped away using a tissue; and
a skip special management step in which a gel cream is uniformly applied over the face, a low frequency wave vibration key is pressed, an operation time and operation intensity are adjusted based on the type of skin, the massage is performed from a lower portion to an upper portion and from an inner portion to an outer portion along a skin pattern, and when the operation time is passed and an alarming sound is outputted, the cream is wiped away using a towel containing a warm water.

11. The method of claim 10, wherein said skip special management step includes a step in which a ultrasonic wave gel is uniformly applied over a face, and the ultrasonic wave key is pressed, and the massage is performed along a skin pattern.

12. The method of claim 10, wherein said each step is performed based on the mode selected in accordance with an input of the user's mode key among the following modes of:
a manual selection mode in which as soon as a desired function is pressed without using a start key for performing a function of each step, a corresponding function is started;
an automatic mode in which when the type of skin is determined in the skin state check step and a certain course is determined based on the type of the skin, each function is automatically performed based on the selected course; and
a fuzzy mode in which a function-based operation time and operation sequence are automatically performed based on a stored program based on a result of the skin checked in the skin state check step.

13. The method of claim 12, wherein said manual selection mode includes:
a step in which when an external input of a skin check key is detected, a certain jig which will be used for a skin check is displayed on a LCD(Liquid Crystal Display) panel of the display unit;
a step in which when a user starts to check a skin using the displayed jig, a skin check data is received from the jig which is adapted for checking the skin, and a result of the skin check is computed;
a step in which a skin type, skin check value and graph which are obtained based on a result of the skin check are displayed at a certain portion of the LCD panel of the display unit;
a step in which when a user inputs a certain key among the far infrared ray key, purification key, low frequency wave(−) key, low frequency wave(□) key, low frequency wave vibration key and ultrasonic wave key based on the type of the skin, the inputted key is detected, and a corresponding function corresponding to the inputted key is performed, so that the manual mode is implemented; and a step in which a corresponding function is performed, and the function-based operation time, operation intensity, and the selected jig and cosmetics which will be used, are displayed at a certain portion of the LCD panel of the display unit in character and graphic.

14. The method of claim 12, wherein said automatic mode includes:

a step in which when an external input of a skin check key is detected, a jig which will be used for a skin check is displayed on a screen of a LCD panel of the display unit;

a step in which when a user starts to check a skin using the displayed jig, a skin check data is received from the jig which performs a skin check, and a result of a skin check is computed;

a step in which a skin type, skin check value and graph obtained based on a result of the skin check are displayed at a certain portion of the LCD panel of the display unit;

a step in which when a user's automatic key input is detected, the automatic mode is activated, and the number of the user's automatic key inputs is detected;

a step in which when the automatic key is inputted one time, a function-based course corresponding to a dry skin is automatically designated, and when the automatic key is inputted two times, a function-based course corresponding to a neutral skin is automatically designated, and the automatic key is inputted three times, a function-based course corresponding to an oily skin is automatically designated;

a step in which the jig and cosmetics which will be used for a function in the operation step in accordance with an automatically designated function-based course are flickered for thereby displaying a function which is in the current standby mode; and a step in which a start key input is detected and a construction unit is controlled for thereby performing a corresponding function.

15. The method of claim 12, wherein said fuzzy mode includes:

a step in which when an input of a user's fuzzy key is detected, the fuzzy mode is activated, and the fuzzy mode and a jig which will be used for a skin check are displayed on a LCD panel of the display unit in accordance with an input of the user's fuzzy key;

a step in which when a user starts a skin check using the displayed jig, a skin check data is received from the jig which performs the skin check, and a result of the skin check is computed;

a step in which a skin type, skin check value and graph obtained based on a result of the skin check are displayed at a certain portion of the LCD panel of the display unit;

a step in which a function-based course is automatically designated based on the determined skin type, and the automatically designated function-based courses are sequentially displayed, and a function-based operation time, operation intensity and jig and cosmetics which will be used, are displayed at a certain portion of the LCD panel of the display unit in character and graphic;

a step in which the jig and cosmetics which will be used for a function in the operations step flickered based on the automatically designated function-based course for thereby displaying a function which is in the current standby mode; and a step in which an input of the start key is detected, and a construction unit is controlled for thereby performing a corresponding function.

16. The method of claim 12, wherein said each mode includes:

a step in which an input of a user's time adjusting key and intensity adjusting key is detected, an operation time and operation intensity of the current operating function are adjusted;

a step in which when there is an input of an operation stop/cancel key, the current operating function is temporarily stopped and cancelled; and a step in which the temporarily stopped function is restarted in accordance with an input of the start key.

17. The method of claim 13, further comprising:

a step in which a connection state of the ultrasonic wave jig is detected, and when the ultrasonic wave jig is connected as a result of the detection, a massage portion is selected in accordance with the number of inputs of a user's ultrasonic wave key and is displayed at a certain portion of the LCD panel of the display unit; and a step in which when the ultrasonic wave key is inputted one time, a massage portion, operation time and cosmetics which will be used, are displayed, so that a corresponding ultrasonic wave massage is performed for thereby massaging a face, and when the ultrasonic wave key is inputted two times, a massage portion, operation time and cosmetics which will be used, are displayed, so that a corresponding ultrasonic wave massage is performed for thereby massaging a body portion.

* * * * *